(12) United States Patent
Lee (10) Patent No.: US 8,088,775 B2
(45) Date of Patent: Jan. 3, 2012

(54) PHARMACEUTICAL COMPOSITION FOR TREATING HAIR LOSS

(76) Inventor: Eun-Joo Lee, Daejeon (KR)

( * ) Notice: Subject to any disclaimer, the term of this patent is extended or adjusted under 35 U.S.C. 154(b) by 99 days.

(21) Appl. No.: 12/722,720

(22) Filed: Mar. 12, 2010

(65) Prior Publication Data

US 2010/0222364 A1    Sep. 2, 2010

Related U.S. Application Data (62) Division of application No. 11/547,574, filed as application No. PCT/KR2005/001063 on Apr. 13, 2005, now abandoned.

(30) Foreign Application Priority Data

Apr. 14, 2004  (KR) .................. 10-2004-0025869
Apr. 8, 2005   (KR) .................. 10-2005-0029495

(51) Int. Cl.
*A61K 31/495*    (2006.01)

(52) U.S. Cl. ................................. 514/252.12

(58) Field of Classification Search .............. 514/252.12
See application file for complete search history.

(56) References Cited

U.S. PATENT DOCUMENTS

| | | |
|---|---|---|
| 4,139,619 A | 2/1979 | Chidsey, III |
| 4,377,584 A | 3/1983 | Rasmusson et al. |
| 4,525,358 A | 6/1985 | Baltes et al. |
| 4,760,071 A | 7/1988 | Rasmusson et al. |

FOREIGN PATENT DOCUMENTS

| | | |
|---|---|---|
| EP | 0 200 406 A2 | 12/1986 |
| EP | 1346983 | 9/2003 |
| JP | 05-058851 | 3/1993 |
| JP | 07-267830 | 10/1995 |
| JP | 07-277930 | 10/1995 |
| JP | 7316022 | 12/1995 |
| KR | 2000-0075651 | 9/1998 |
| KR | 2003-0022763 A1 | 5/2001 |
| KR | 100311199 | 9/2001 |
| KR | 1020030025669 A | 3/2003 |
| KR | 2003-0042504 | 6/2003 |
| KR | 20040016559 | 2/2004 |
| KR | 100415858 B1 | 6/2004 |
| KR | 200440087811 | 10/2004 |
| WO | 9400442 | 1/1994 |
| WO | 03002098 A1 | 1/2003 |

OTHER PUBLICATIONS

Holt et al., "Inhibition of Steroid 5α-Reductase by Unsaturated 3-Carboxysteroids", J. Med. Chem., 1990, p. 943-950, vol. 33.

M.R. Namazi, "Cetirizine and Allopurinol as Novel Weapons Against Cellular Autoimmune Disorders", International Immunopharmacology, 2004, p. 349-353, vol. 4.

Morissette et al., Advanced Drug Delivery Reviews, 2004, vol. 56, pp. 275-300.

Vippagunta et al., Advanced Drug Delivery Reviews, 2001, vol. 48, pp. 2-26.

*Primary Examiner* — Phyllis G. Spivack
*Assistant Examiner* — Nelson Blakely, III
(74) *Attorney, Agent, or Firm* — The Webb Law Firm (57) ABSTRACT

Disclosed is the use of 2-[2-[4-[(4-chlorophenyl)phenylmethyl]-1-piperazinyl]ethoxy]-acetic acid or its pharmaceutically acceptable salt for the reduction of hair loss; for hair regrowth, hair toning and hair growth; and for the treatment of female hirsutism.

6 Claims, 5 Drawing Sheets

PHARMACEUTICAL COMPOSITION FOR TREATING HAIR LOSS

CROSS REFERENCE TO RELATED APPLICATIONS

This application is a divisional of co-pending U.S. patent application Ser. No. 11/547,574, filed Oct. 3, 2006, which is the United States National Stage Under 35 U.S.C. §371 of International Application No. PCT/KR2005/001063, filed on Apr. 13, 2005.

TECHNICAL FIELD

The present invention is related to an oral pharmaceutical composition having the effects of the prevention of hair loss, epilation, hair toning, and hair growth, as well as the prevention of female hirsutism and benign prostatic hyperplasia, of which effective component is 2-[2-[4-[(4-chlorophenyl)phenylmethyl]-1-piperazinyl]ethoxy]-acetic acid, or its pharmaceutically acceptable salt, hydrate, or solvate.

BACKGROUND ART

Several theories have been presented for the reasons for hair loss including the theory of inferior blood circulation, excessive actions of a male hormone, excessive secretion of sebum, lowering of scalp functions due to dandruff and other bacteria, genetic factors, aging stress, etc. However, nothing has been clarified for the reasons for hair loss until the present time. Moreover, recently, the population suffering from hair loss due to changes in eating habits, increase in stress by social environment, etc. has been on the increasing trend, the ages of such population have been younger, and the female population of hair loss has been increased.

Among the above reasons for hair loss, the most frequently seen type of hair loss which is directly related to the excessive secretion of a male hormone is androgenic alopecia, called male pattern baldness usually. A male having androgenic alopecia shows phenomena that his healthy hairs become thinner, shorter, and weaker gradually, and readily broken. These phenomena are called miniaturization, during which hair follicles become thinner, unnoticeable, and changed to short downy hair eventually leading to hair loss. Accordingly, recently, many studies on the prevention and treatment of hair loss through the suppression of activities of a male hormone have been reported.

Male pattern baldness, which is the most frequently seen type of hair loss, is induced as testosterone, one of male hormones, is converted into dihydrotestosterone (DHT), which is an active-type male hormone, by $5^\alpha$-reductase, and thus activated dihydrotestosterone is combined with an androgen receptor making the synthesis of proteins of follicular cells delayed, the growing period of follicles shortened, and follicles shrunk. Also, sebum may be produced excessively during the process of androgenic alopecia, and as a result, hair loss accompanied by inflammation may be shown on the scalp [Dennis A Holt et al., J. Med. Chem., 33, 943 (1990)].

In the meantime, it has been known that there have been more various reasons for female hair loss compared with those for male hair loss. But in reality, androgenic alopecia generated as the sensitivity to the male hormone is inherited occupies about 50% of hair loss of adult females.

The mechanism of male pattern baldness coming from the excessive production of dihydrotestosterone by the actions of $5\alpha$-reductase suggests that it is possible to prevent and treat effectively androgenic alopecia by using anti-androgenic activation effects suppressing the activities of $5\alpha$-reductase or the combination with an androgenic receptor, or by using the actions of estrogen conversion acceleration of androgen.

The treatment drug proposed based on the above theoretical basis is Propecia (of which main component is finasteride) manufactured and sold by Merck & Co., Inc. of the U.S.A. Finasteride shows a mechanism of suppressing the conversion of testosterone, which is a male hormone, to dihydrotestosterone, which is a strong active-type male hormone. It has been the only oral treatment drug on the market of the world since it was approved by FDA of the U.S. as a treatment agent of active-type hair loss in 1997 (U.S. Pat. Nos. 4,377,584 and 4,760,071, Korean Patent No. 10-0415858, Korean Laid-Open Patent No. 2003-0042504). And yet, Propecia is disadvantageous in that its effects are shown several months after it is administered, there are side effects such as diminution of sexuality, impotence, etc., it may be used only for males, and safety for being used for females and children is not established presently, and its use for pregnant women or fertile women is strictly prohibited.

Further, the most widely used formulation for the treatment or prevention of hair loss is Minoxidil (6-(1-piperidinyl-2,4-pyrimidineamine-3-oxide) (U.S. Pat. No. 4,139,619) developed by Pharmacia Sverige AB and approved by FDA of the U.S. as a drug accelerating re-growth of hair. Minoxidil has been a vasodilation ($K^+$) channel opener for the treatment of high blood pressure acting as a smooth muscle vasodilator, but became more famous as an epilation drug as an epilation phenomenon has been shown as a side effect in using it. This drug has been somewhat effective (20 ?30%) when it has been applied externally to young people or people having oily hair or people having the whirl of hair on the head fallen out, but in other cases, not only it has shown insignificant effects but also there have been reported some side effects such as contact dermatitis, dried mouth, lowering of blood pressure, dizziness, etc., but also it has been troublesome to use it since it has had to be used a few times every day. Besides the above, hair tonics containing hyperosmotic extracts, hair-growing agents, epilation prevention agents containing hyperosmotic extracts, and the mechanism of the actions of $5\alpha$-reductase have been disclosed (Japanese Laid-Open Patents Nos. PYUNG7-267830, PYUNG7-277930, and PYUNG5-58851, Korean Patent No. 10-0311199).

Still further, among diseases induced due to an excessive amount of dihydrotestosterone, particularly, benign prostatic hyperplasia (BPH) is shown in proportion to the ages of males who are older than 50 years old and brings about pain coming from dysuria due to pressing of urinary tract. Causal treatment of this disease is available through the ectomy of enlarged prostatic tissues. However, since most of patients has been aged making the objects of operation limited and there have been problems of side effects, recurrence, etc. after operation, expectation for simple drug therapies has been increased.

$5\alpha$-reductase inhibitor has been recognized as a safe and causal treatment agent of benign prostatic hyperplasia since it has been possible to treat urination impairment by reducing enlarged prostate gland without any side effects found in anti-male-hormone drugs by showing the anti-androgenic activity effects by selectively suppressing the production of dihydrotestosterone without affecting testosterone showing the actions of a male hormone. Therefore, the compounds such as finasteride (product name is Proscar manufactured and sold by Merck Pharmaceutical Company) suppressing the production of dihydrotestosterone in tissues by hindering the actions of this $5\alpha$-reductase is on the market and used currently as a treatment agent of benign prostatic hyperplasia (U.S. Pat. Nos. 4,377,584 and 4,760,071, Korean Laid-Open Patents Nos. 2003-22763, 2000-0075651, and 2004-0016559).

In the meantime, a pharmaceutical composition of which effective component is 2-[2-[4-[(4-chlorophenyl)phenylmethyl]-1-piperazinyl]ethoxy]-acetic acid (chemical formula is $C_{21}H_{25}ClN_2O_3$, molecular weight is 388) of the present invention and its pharmaceutically acceptable salt has been on the market as an anti-allergic agent, anti-histamine agent, bronchodilator, and spasmolytic and known to be an FDA-approved product having no side effects and superior safety. However, nothing has been reported up to the present time as to where it might have been used as a useful active component for the prevention of baldness and fall-out of hairs, epilation, hair toning, hair growth, and the treatment of female hirsutism, benign prostatic hyperplasia, or the like, which are the objects of the present invention.

SUMMARY OF THE INVENTION

The inventors of the present invention found out that a pharmaceutical composition of 2-[2-[4-[(4-chlorophenyl) phenylmethyl]-1-piperazinyl]ethoxy]-acetic acid, or its pharmaceutically acceptable salt, hydrate, or solvate as an active component is effective for the prevention of hair loss, epilation, hair toning, hair growth, as well as the treatment of female hirsutism and benign prostatic hyperplasia, and completed the present invention including the above active components.

It is, therefore, an object of the present invention to provide with a composition having 2-[2-[4-[(4-chlorophenyl)phenylmethyl]-1-piperazinyl]ethoxy]-acetic acid, or its pharmaceutically acceptable salt, hydrate, or solvate as an effective component, and further, to provide with a pharmaceutical composition having 2-[2-[4-[(4-chlorophenyl)phenylmethyl]-1-piperazinyl]ethoxy]-acetic acid, or its pharmaceutically acceptable salt, hydrate, or solvate which has the effects of prevention of hair loss, suppression of excessive production of sebum, epilation during which new hairs are generated, hair toning during which thin and weak hairs are changed to be thick and strong, and hair growth during which young hairs are grown well, and superior activities for the treatment of female hirsutism and benign prostatic hyperplasia. Another object of the present invention is to provide with an orally administered pharmaceutical composition which is in the most readily administered form; effective for the prevention of hair loss, and for epilation, hair toning, and hair growth; and useful for the treatment of benign pro static hyperplasia.

In more detail, the present invention is characterized by an orally administered pharmaceutical composition which is effective for the prevention of hair loss, and for epilation, hair toning, and hair growth, and for the treatment of female hirsutism and benign prostatic hyperplasia, of which effective component is 2-[2-[4-[(4-chlorophenyl)phenylmethyl]-1-piperazinyl]ethoxy]-acetic acid shown in the following Chemical Formula 1, or its pharmaceutically acceptable salt, hydrate, or solvate.

The composition of the present invention is advantageous in that it is a non-steroidal composition and has no side effects such as sexual function disorder, etc. shown in the conventional treatment agents of diseases related to hair loss.

[Chemical Formula 1]

Although 2-[2-[4-[(4-chlorophenyl)phenylmethyl]-1-piperazinyl]ethoxy]-acetic acid shown in the above Chemical Formula 1 and its pharmaceutically acceptable salt have been published to be useful materials for anti-allergic agents, anti-histamines, bronchodilators, and spasmolytics, their somatic stability has been proven, and they have been approved by FDA of the U.S. and on the market, nothing has been reported until the present time as to their uses as useful active components for the prevention of hair loss, effective epilation, and treatment of female hirsutism and benign prostatic hyperplasia. The pharmaceutical composition having 2-[2-[4-[(4-chlorophenyl)phenylmethyl]-1-piperazinyl]ethoxy]-acetic acid, or its pharmaceutically acceptable salt, hydrate, or solvate having anti-androgenic active effects according to the present invention as effective components bring about the prevention of fall-out of hairs and an effect of epilation, or rapidly recover the prostate gland to its original state.

The pharmaceutically acceptable composition for the prevention of baldness and fall-out of hairs and for epilation in the present invention refers to a composition that can prevent fall-out of hairs and baldness through the administration of the composition according to the present invention for the prevention of baldness and fall-out of hairs. More concretely, the effects of the prevention of fall-out of hairs and baldness refers to the effects of the prevention of hair loss, epilation, promotion of growth of hair, toning of hair, growth of hair, softness, and suppression of an excessive production of sebum. The hairs to which the composition of the present invention is applied include all parts of human bodies where there are hair roots and follicles such as the hair roots and follicles on the head, hair on the head, inner and outer eyelashes, mustache, hair of the armpit, and pubic hair.

In the present invention, the pharmaceutical composition for the treatment of benign prostatic hyperplasia refers to a composition that can cure benign prostatic hyperplasia through the administration of the pharmaceutical composition according to the present invention for the treatment of benign prostatic hyperplasia induced due to an excessive amount of dihydrotestosterone. More concretely, such effect of treatment of benign prostatic hyperplasia means curing of the enlarged prostate gland to have its original size.

2-[2-[4-[(4-chlorophenyl)phenylmethyl]-1 piperazinyl] ethoxy]-acetic acid, which is an active component of the pharmaceutical composition according to the present invention includes its (+)- and (−)-optical isomers and their racemates.

Also, pharmaceutically acceptable salts of 2-[2-[4-[(4-chlorophenyl)phenylmethyl]-1-piperazinyl]ethoxy]-acetic acid may include its organic and inorganic acids as well as the solvates and hydrates of the above salt compounds. Pharmaceutically acceptable acid-added salts include the compounds formed from hydrochloric acid, bromic acid, sulfuric acid, citric acid, tartaric acid, phosphoric acid, lactic acid, pyruvic acid, acetic acid, trifluoroacetic acid, triphenylacetic acid, phenylacetic acid, substituted phenylacetic acid, for example, methoxyphenylacetic acid, sulfaminic acid, sulfanilic acid, succinic acid, oxalic acid, fumaric acid, maleic acid, malic acid, glutamic acid, aspartic acid, oxaloacetic acid, methanesulfonic acid, ethanesulfonic acid, arylsulfonic acid (for example, p-toluenesulfonic acid, benzenesulfonic acid, naphthalenesulfonic acid or naphthalenedisulfonic acid), salicylic acid, glutaric acid, gluconic acid, tricarballylic acid, mandelic acid, cinnamic acid, substituted cinnamic acid, ascorbic acid, oleic acid, naphthoic acid, hydroxynaphthoic acid (for example, 1- or 3-hydroxy-2-naphthoic acid), naphthaleneacrylic acid, benzoic acid, 4-methoxybenzoic acid, 2- or 4-hydroxybenzoic acid, 4-chlorobenzoic acid, 4-phenylbenzoic acid, benzeneacrylic acid, and isethionic acid.

More concretely, 2-[2-[4-[(4-chlorophenyl)phenylmethyl]-1-piperazinyl]ethoxy]-acetic acid dichlorates and monochlorates may be examples of the above.

The amount of the compound shown in Chemical Formula 1 or its pharmaceutically acceptable salt used to achieve therapeutic effects according to the present invention may naturally differ according to the nature of the compound, method of administration, object to be treated, and disease to be treated. However, based on 2-[2-[4-[(4-chlorophenyl)phenylmethyl]-1-piperazinyl]ethoxy]-acetic acid, which is the active compound according to the present invention, and its pharmaceutically acceptable salt, the amount of use is usually 1 to 2,000 mg per day for an adult, preferably, 5 to 300 mg per day for an adult, and it can be administered orally or locally according to its formulation type.

For the oral administration of the pharmaceutical composition according to the present invention, it can be manufactured in various forms known conventionally, i.e., in the forms of tablets, powders, dried syrups, chewable tablets, granules, chewing tablets, capsules, soft capsules, pills, drinks, sublingual tablets, etc.

If it is manufactured in the form of powder, it is preferable to apply its content reasonably according to the type of formulation such as the amount of the effective component of 0.01 to 99.90 weight % or the like.

In whichever form the pharmaceutical composition according to the present invention is manufactured, if the amount of 2-[2-[4-[(4-chlorophenyl)phenylmethyl]-1-piperazinyl]ethoxy]-acetic acid or its pharmaceutically acceptable salt exceeds the maximum total weight, it may be difficult to maintain its physical properties; and if it is less than the minimum weight, the effects of prevention of hair loss and improvement of hairs by the active component may not be shown sufficiently.

The tablets according to the present invention may be administered to patients in arbitrary forms or methods in which their effective amount has bio-availability, i.e., through an oral pathway. In which form or method they may be administered properly may be selected according to the characteristics of the state of the disease to be cured, stage of the disease, and other related circumstances. Also, the tablets may have one or more pharmaceutically acceptable fillers (vehicles), where the ratio and properties of such filler(s) are determined according to the solubility and chemical properties of the tablet selected, the path of administration selected, and standard practice of pharmaceutics.

In more detail, the composition according to the present invention may include a therapeutically effective amount of the above-described active component as an essential component along with one or more pharmaceutically acceptable fillers.

Fillers may be solid or semi-solid materials that can function as the vehicles or media of the active component, and which fillers are proper is widely known in the art.

Fillers may be selected in relation to the intended form of administration. More concretely, in cases of tablets, powders, chewable tablets, granules, chewing tablets, capsules, soft capsules, pills, sublingual tablets, or syrup forms, their therapeutically active drug components may be mixed with arbitrary oral non-toxic pharmaceutically acceptable inactive fillers such as lactose, starch, etc. Arbitrarily, the pharmaceutical tablets of the present invention may also contain binders such as non-crystalloid cellulose, gum tragacanth, or gelatin; disintegrating agents such as alginic acid; lubricants such as magnesium stearate; glidants such as colloidal silicon dioxide; sweeteners such as sucrose or saccharin; coloring agents or flavoring agents such as peppermint, methyl salicylate, and the like.

Tablet forms may be the most advantageous oral unit formulations since it is easy to administer them. If necessary, tablets may be coated with sugars, shellac, or other enteric coating agents, and it is preferable that each tablet or capsule contains about 10 to 200 mg of the effective component.

The composition according to the present invention has a proven bio-stability throughout the world as an anti-allergic agent, anti-histamine, bronchodilator, and spasmolytic, but nothing has been reported until the present time as to its effects for the prevention of hair loss in androgenic alopecia, epilation, hair toning, hair growth, and female hirsutism, and the treatment of benign prostatic hyperplasia, which are the uses of the present invention. It is shown from the results of clinical experiments and in-vivo experiments using animals determining direct effects of the composition that the composition of the present invention is advantageous in that it has very superior activities for the prevention of hair loss, epilation, hair toning, hair growth, and female hirsutism, and for the treatment of benign prostatic hyperplasia; its safety is secured since active components, which are proven to be harmless to human bodies, are used; it is very easy to use the composition compared to applicable formulations owing to simple ways of administration such as oral administration; it is very convenient to use it since sufficient effects may be expected by administering once a day simply; it contains non-steroidal active materials; and there are shown no side effects such as sexual function disorder, etc. shown in the conventional oral epilation agents and prostatic hyperplasia treatment agents.

Further, the composition of the present invention is a safe composition having no problem of side effects reported yet in spite of its long-term use, which means that it conforms to the temporal trend in which it is critically necessary to have treatment agents for hair loss and diseases related to the prostate gland.

BRIEF DESCRIPTION OF DRAWINGS

A more complete appreciation of this invention, and many of the attendant advantages thereof will be readily apparent as the same becomes better understood by reference to the following detailed description when considered in conjunction with the accompanying drawings, wherein.

The present invention is illustrated in greater detail by means of the following examples:

For a compound in the comparative group, finasteride, which is known to be the suppressant of testosterone 5α-reductase and an active material showing superior effects for the prevention of hair loss in androgenic alopecia and the treatment of benign prostatic hyperplasia, is used.

4-week-old male SD rats are acclimated for one week and castrated, and assigned to each of the solvent control group; prostatic hyperplasia inducement group through the stimulation with a hormone; experimental group to which 2-[2-[4-[(4-chlorophenyl)phenylmethyl]-1-piperazinyl]ethoxy]-acetic acid dihydrochloride, which is a compound according to the present invention, is administered to reduce the prostate gland after prostatic hyperplasia inducement through the stimulation with a hormone; and comparative group to which finasteride is administered. The weight of prostate glands of the solvent control group (23.3±1.5 mg) is used for that of the control group in order to compare the results of other groups, and detailed experimental methods of administration of compositions are summarized in the following Table 1:

TABLE 1

Methods of administration of castrated male SD rats for the observation of anti-androgenic active effects

| Classification | Administered materials | Daily dose (hypodermic injection + oral administration) | Remarks |
| --- | --- | --- | --- |
| Solvent control group | Cotton seed oil | 0.2 mL + 2 mL | In all experiments, the administration of TP, DHTP, and the composition is performed under the same conditions as those of the solvent control group. |
| Prostatic hyperplasia inducement group | TP | 10 μg + 2 mL | |
| | DHTP | 20 μg + 2 mL | |
| Comparative group | TP + 0.5 mg of finasteride | 10 μg + 0.5 mg | |
| | DHTP + 0.5 mg of finasteride | 20 μg + 0.5 mg | |
| Experimental group | TP + 5 mg of the composition of the present invention | 10 μg + 5 mg | |
| | DHTP + 5 mg of the composition of the present invention | 20 μg + 5 mg | |

Notes:
1) TP refers to testosterone propionate, and DHTP refers to dihydrotestosterone propionate.
2) Only cotton seed oil, which is a vehicle, is administered to the solvent group.
3) In the prostatic hyperplasia inducement group, each of TP and DHTP is dissolved in 0.2 mL of cotton seed oil and injected hypodermically in order to induce the stimulation of a hormone, and a vehicle is administered orally in an amount of 2 mL.
4) Also in the comparative group and experimental group, each of TP and DHTP is dissolved in 0.2 mL of cotton seed oil and administered hypodermically, and the drug to be administered is dissolved in 2 mL of cotton seed oil and administered orally.
5) In order to determine effectiveness of the average experimental value of each individual group, 10 male SD rats are assigned to each individual group.

EXAMPLE 1

In-Vivo Experiment for the Observation of Anti-Androgenic Active Effects of Castrated Male SD Rats (1)

In-vivo experiments are performed in order to confirm that 2-[2-[4-[(4-chlorophenyl)phenylmethyl]-1-piperazinyl]ethoxy]-acetic acid, which is the active component of the compound of the present invention, and its pharmaceutically acceptable salt act as anti-androgenic active materials.

Figure 1:
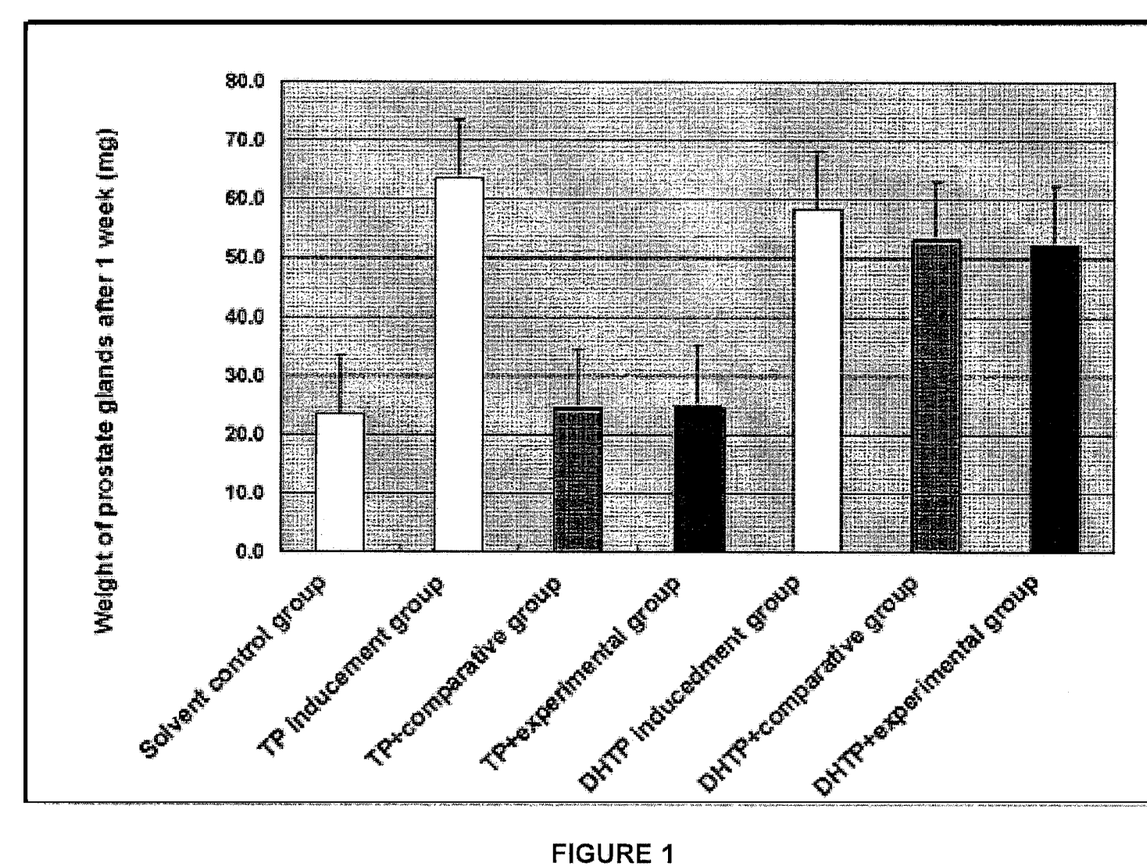
FIG. 1 is a graph showing the changes in the average weight of prosate glands of castrated male SD rats one week after the oral administration of the composition of the present invention in order to measure its anti-androgenic active effects.
Figure 2:
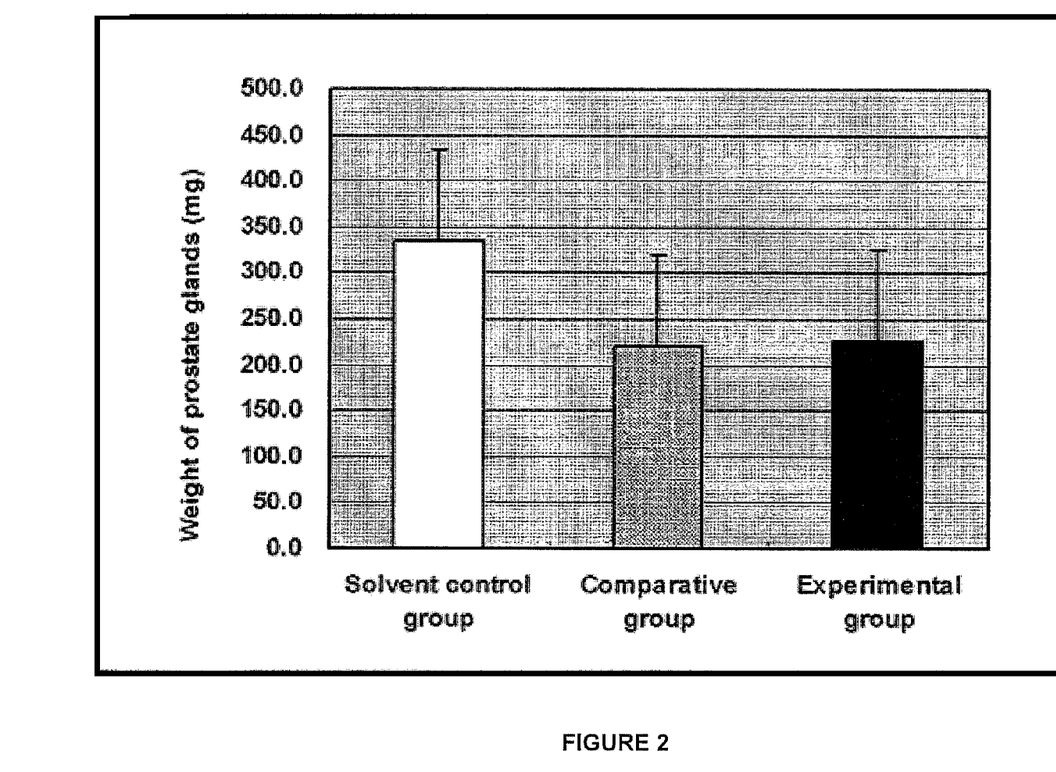
FIG. 2 is a graph showing the changes in the average body weight of castrated male SD rats one week after the oral administration of the composition of the present invention.

Each compound is administered orally continuously for one week according to the method of administration shown in Table 1, prostate glands are removed from the rats in each group while watching, and their weights are measured. The changes in the average weight of prostate glands and the average body weight of castrated male SD rats obtained from the results of experiments are shown in Tables 2 and 3, and the results based on Tables 2 and 3 are shown in FIGS. 1 and 2.

TABLE 2

Changes in the average weight of prostate glands of castrated male SD rats after one week

| Classification | Solvent control group | TP inducement group | TP + comparative group | TP + experimental group | DHTP inducement group | DHTP + comparative group | DHTP + experimental group |
|---|---|---|---|---|---|---|---|
| Average weight (mg) | 23.3 | 63.6 | 24.5 | 25.1 | 58.4 | 53.1 | 52.2 |
| Standard deviation | 1.5 | 3.2 | 1.6 | 1.3 | 2.0 | 1.4 | 1.1 |

TABLE 3

Changes in the average body weight of castrated male SD rats after one week

| Classification | Solvent control group | TP inducement group | TP + comparative group | TP + experimental group | DHTP inducement group | DHTP + comparative group | DHTP + experimental group |
|---|---|---|---|---|---|---|---|
| Average weight (mg) | 122.1 | 126.7 | 112.6 | 113.4 | 118.7 | 119.6 | 117.1 |
| Standard deviation | 12.5 | 7.2 | 8.1 | 8.9 | 13.1 | 9.4 | 9.0 |

As seen in FIG. 1, it is shown that prostatic hyperplasia is evidently induced (63.6±3.2 mg, 58.4±2.0 mg) through the stimulation of a hormone by TP or DHTP in the prostatic hyperplasia inducement group, and similar results of experiments are shown in comparative groups and experimental groups. The average weight of prostate glands of the comparative group to which fmasteride is administered, or of the experimental group to which a pharmaceutical composition having 2-[2-[4-[(4-chlorophenyl)phenylmethyl]-1-piperazinyl]ethoxy]-acetic acid dihydrochloride, which is the composition according to the present invention, as an effective component, after inducing enlargement of prostate glands with TP (24.5±1.6 mg, 25.1 ?1.3 mg) shows an almost similar value to the weight of prostate glands of the solvent control group to which only vehicles are administered (23.3±1.5 mg), which means that the enlarged size of prostate glands is recovered to the normal size and there are assured effects of treatment. However, even if finasteride is administered to the comparative group or the composition of the present invention to the experimental group, the weight of prostate glands after inducement with DHTP (58.4±2.0 mg) is not greatly affected by the above administration (53.1±1.4 mg, 52.2±1.1 mg).

It is shown from these results that, in the comparative group to which finasteride is administered or the experimental group to which the composition of the present invention is administered, the size of prostate glands enlarged by the inducement with TP is reduced to the normal size and is not affected by the inducement with DHTP. It is also shown that the composition according to the present invention has a similar efficacy to that of finasteride which is administered to the comparative group.

The above results imply that the composition according to the present invention acts as an anti-androgenic active material, and may be effective for the treatment of androgenic alopecia or benign prostatic hyperplasia through such mechanism.

EXAMPLE 2

In-Vivo Experiment for the Observation of Anti-Androgenic Effects of Normal Male SD Rats (2)

Figure 3:
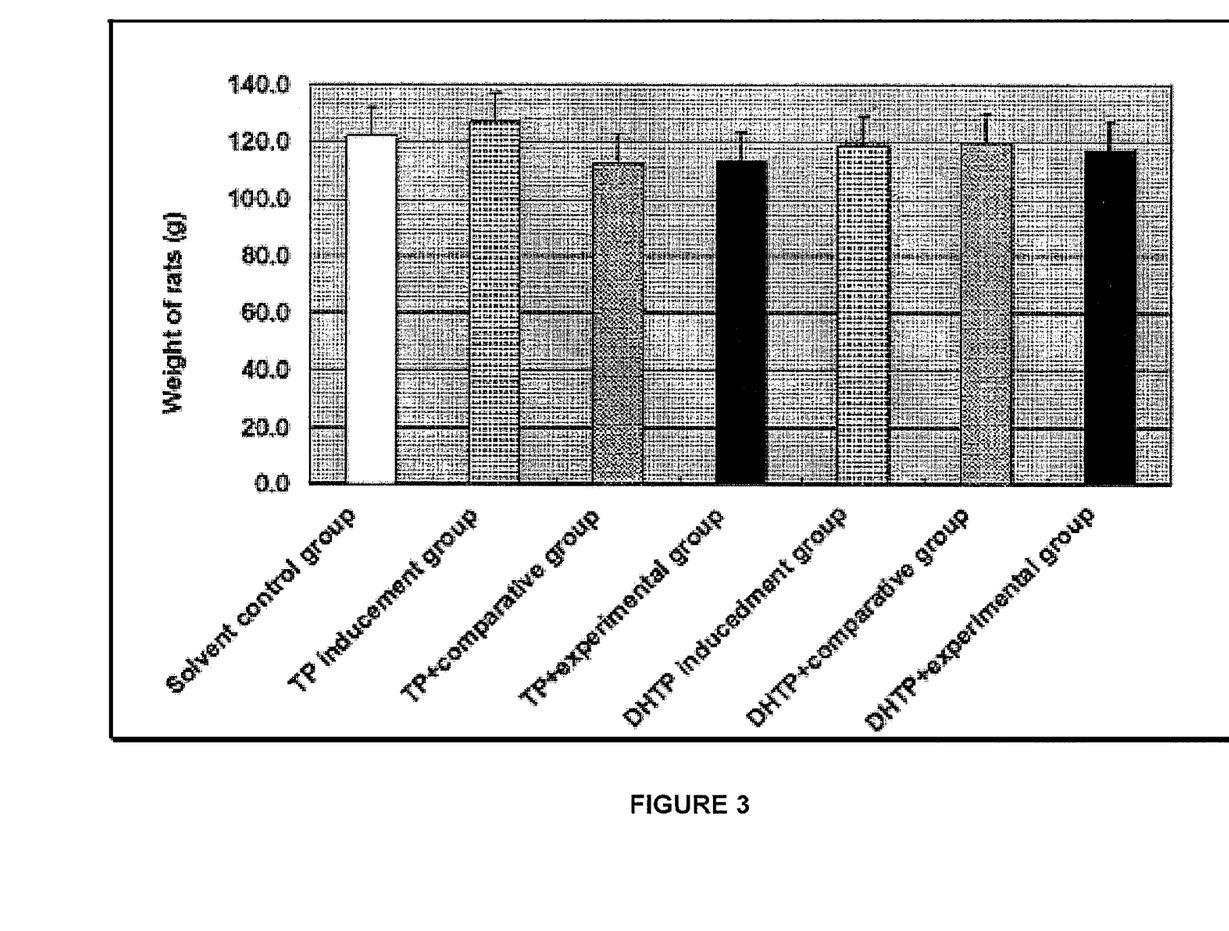
FIG. 3 is a graph showing the changes in the average weight of prostate glands of normal male SD rats two weeks after the oral administration of the composition of the present invention in order to measure its anti-androgenic active effects.
Figure 4:
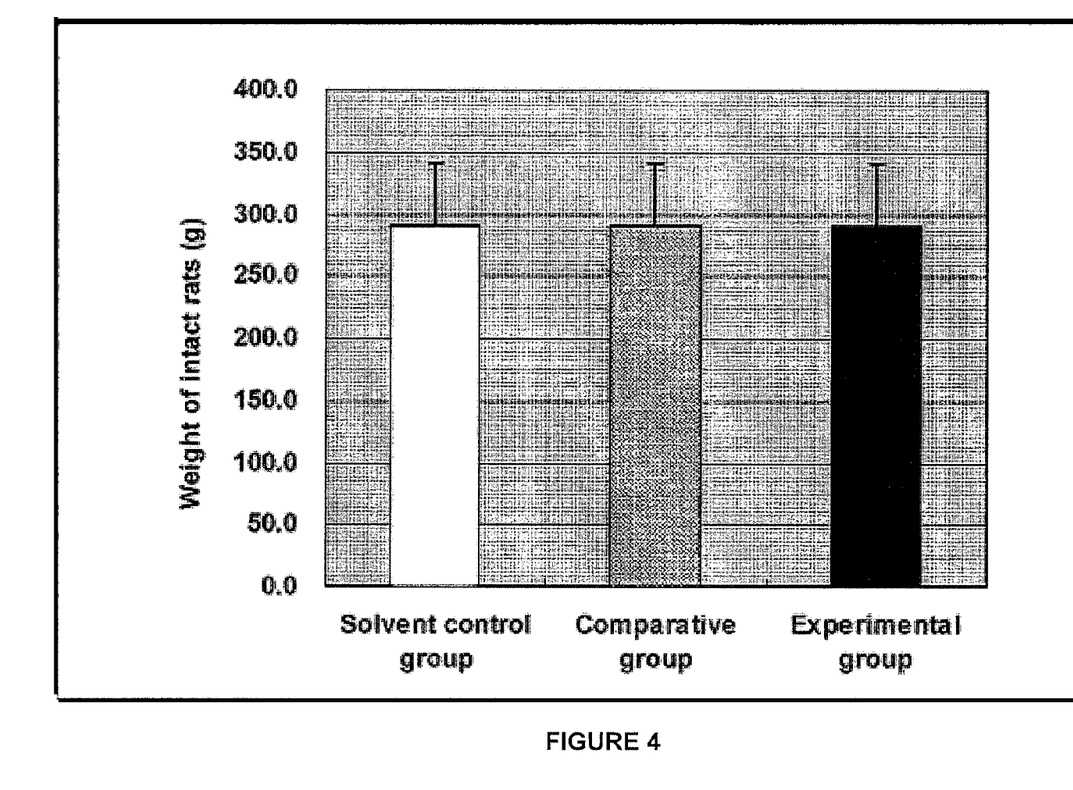
FIG. 4 is a graph showing the changes in the average body weight of normal male SD rats two weeks after the oral administration of the composition of the present invention.

Experiments to determine whether prostate glands are reduced materially are performed by administering orally for two weeks continuously finasteride and the composition of the present invention, of which effective component is 2-[2-[4-[(4-chlorophenyl)phenylmethyl]-1-piperazinyl]ethoxy]-acetic acid dihydrochloride to normal 8-week-old SD rats. As in Example 1, 10 normal SD rats are assigned to each individual group, only cotton seed oil which is a vehicle is administered to the solvent control group, and fmasteride and the composition of the present invention are administered orally to the comparative and experimental groups under the same conditions. After the experiments are completed, the changes in the weight of prostate glands removed from normal SD rats and the changes in the weight of normal SD rats measured are shown in Tables 4 and 5 and diagrammatized in FIGS. 3 and 4. FIG. 3 shows that the weight of prostate glands of the rats in the comparative group to which finasteride is administered and the experimental group to which the composition of the present invention is administered is significantly lower than the weight of prostate glands of the rats in the solvent control group to which only vehicles are administered. These results, along with the experimental results of Example 1, prove that fmasteride and the composition of the present invention are effective for the treatment of androgenic alopecia and useful for the treatment of benign prostatic hyperplasia.

TABLE 4

Changes in the average weight of prostate glands of normal male SD rats after the administration of drugs for 2 weeks

| Classification | Solvent control group | Comparative group | Experimental group |
|---|---|---|---|
| Average weight (mg) | 333.8 | 220.0 | 226.7 |
| Standard deviation | 79.8 | 35.4 | 37.3 |

TABLE 5

Changes in the average body weight of normal male SD rats after the administration of drugs for 2 weeks

| Classification | Solvent control group | Comparative group | Experimental group |
|---|---|---|---|
| Average weight (mg) | 291.5 | 290.7 | 291.4 |
| Standard deviation | 6.6 | 6.8 | 6.9 |

EXAMPLE 3

Clinical Experiment to Study Effects for the Prevention of Hair Loss, and for Hair Toning and Hair Growth (1)

Into a rotary mixer, 100 parts by weight of a pharmaceutical composition of which effective component is 2-[2-[4-[(4-chlorophenyl)phenylmethyl]-1-piperazinyl]ethoxy]-acetic acid dihydrochloride, 100 parts by weight of b-cyclodextrin, 2 parts by weight of the liquorice flavoring agent, and 800 parts by weight of mannitol are put, granulated with water, and extruded. The extruded material thus obtained is dried in the floating air layer. The therapeutical efficacy for the prevention of hair loss is experimented clinically by using thus obtained extruded material as shown in Tables 6 and 7. The objects of clinical experiments are selected based on 35 male and female healthy adults older than 20 years old who suffer from symptoms of hair loss. The therapeutical efficacy of female hair loss is also tested as females suffering from hair loss are included in the specimen population (including 5 males in the placebo control group). As to the dose, 10 mL of the pharmaceutical composition having 2-[2-[4-[(4-chlorophenyl)phenylmethyl]-1-piperazinyl]ethoxy]-acetic acid dihydrochloride as an effective component, which is an effective dosage amount per day (including 10 mg of the effective component), is administered once a day.

The degree of progression of hair loss and the degree of individual feeling of the strength of hair toning and thickness of hairs after the pharmaceutical composition of the present invention is administered are investigated and evaluated for each individual. In the criteria for determination, greater than 90% shows the degree that hair loss does not occur practically and it may be felt that the strength and thickness of hairs are improved significantly; 60-80% shows a state that the number of hair loss is reduced significantly, and the effect of hair toning is noticeable; 40-60% shows a case that the number of hair loss is reduced by greater than 50% compared to the conventional hair loss; 20-40% shows a case that the number of hair loss is reduced by greater than 30% compared to the conventional hair loss; 10-20% shows a case that the number of hair loss is reduced somewhat and the effect of hair toning is not observed specifically; and no effect shows a case that the reduction of hair loss or improvement on thoughness of hairs is not felt practically.

As shown in Table 6, as to the effect of prevention of hair loss, hair loss is not shown seven days after the administration of the composition in a fast case, and hair loss is prevented in almost all specimens in about three weeks. However, no effects are observed in the control group in which a placebo is administered.

TABLE 6

Evaluation of clinical experiments (1)-(Primary specimens)

| | Time taken for the efficacy to be shown | | | | | | |
|---|---|---|---|---|---|---|---|
| | 3-5 days | 7 days | 14 days | 21 days | 28 days | Minor effect | Total |
| Total | 0 | 7 | 17 | 5 | 0 | 1 | 35 |
| Male | 0 | 6 | 11 | 3 | 0 | 0 | 20 |
| Female | 0 | 1 | 6 | 2 | 0 | 1 | 10 |
| Male in control group (placebo) | 0 | 0 | 0 | 0 | 0 | 5 | 5 |

As shown in Table 7, remarkable effects of the prevention of hair loss are observed both in males and females. However, no effects are observed in the control group to which a placebo is administered, which shows that the therapeutical efficacy of the composition of the present invention for diseases related to hair loss is very superior

TABLE 7

Evaluation of clinical experiments (2)-(Primary specimens)

| | Degree of efficacy | | | | | | |
|---|---|---|---|---|---|---|---|
| | No effect | 10-20% | 20-40% | 40-60% | 60-80% | Greater than 90% | Total |
| Total | 1 | 0 | 0 | 9 | 19 | 1 | 35 |
| Male | 0 | 0 | 0 | 6 | 13 | 1 | 20 |
| Female | 1 | 0 | 0 | 3 | 6 | 0 | 10 |
| Male in control group (placebo) | 5 | 0 | 0 | 0 | 0 | 0 | 5 |

EXAMPLE 4

Clinical Experiment to Study Effects for the Prevention of Hair Loss, and for Hair Toning and Hair Growth (2)

Into a mixer, 100 parts by weight of 2-[2-[4-[(4-chlorophenyl)phenylmethyl]-1-piperazinyl]ethoxy]-acetic acid dihydrochloride, 50 parts by weight of ascorbic acid, 50 parts by weight of corn starch, 50 parts by weight of lactose, 50 parts by weight of crude cellulose, 2 parts by weight of magnesium stearate, 2 parts by weight of a perfume, and 700 parts by weight of mannitol are put, and the mixture is made to be powder in a usual method. Tablets are manufactured to have a diameter of 5 mm and a weight of 110 mg per tablet (containing 10 mg of the effective component) by pounding the powder using a rotary pounding machine. The effect for the prevention of hair loss is investigated by administering the tablets thus manufactured to 20 healthy adult males who are older than 20 years old and selected to be specimens (including 5 males in the placaebo control group) once a day.

TABLE 8

Evaluation of clinical experiments (3) ?(Secondary specimens)

|  | Time taken for the efficacy to be shown | | | | | |
|---|---|---|---|---|---|---|
|  | 3-5 days | 7 days | 14 days | 21 days | 28 days | Minor effect | Total |
| Total | 0 | 1 | 6 | 8 | 0 | 0 | 20 |
| Male | 0 | 1 | 4 | 5 | 0 | 0 | 10 |
| Female | 0 | 0 | 2 | 3 | 0 | 0 | 5 |
| Male in control group (placebo) | 0 | 0 | 0 | 0 | 0 | 5 | 5 |

TABLE 9

Evaluation of clinical experiments (4)-(Secondary specimens)

|  | Degree of efficacy | | | | | |
|---|---|---|---|---|---|---|
|  | No effect | 10-20% | 20-40% | 40-60% | 60-80% | Greater than 90% | Total |
| Total | 0 | 0 | 0 | 5 | 9 | 1 | 20 |
| Male | 0 | 0 | 0 | 3 | 6 | 1 | 10 |
| Female | 0 | 0 | 0 | 2 | 3 | 0 | 5 |
| Male in control group (placebo) | 5 | 0 | 0 | 0 | 0 | 0 | 5 |

As seen in the above Tables 8 and 9, the effects for the prevention of hair loss are shown to be superior within three weeks in all of 15 people, but no effects are shown in the control group to which the remaining placebo is administered. In case of newly coming out hairs, it is shown that their color and thickness are much stronger than those of old hairs. And no one among 15 people, to whom the composition of the present invention is administered, complains about side effects such as sexual function disorder, etc.

EXAMPLE 5

Clinical Experiment to Study Effects for the Prevention of Hair Loss, and for Hair Toning and Hair Growth (3)

Into a mixer, 100 parts by weight of 2-[2-[4-[(4-chlorophenyl)phenylmethyl]-1-piperazinyl]ethoxy]-acetic acid dihydrochloride, 50 parts by weight of ascorbic acid, 50 parts by weight of corn starch, 50 parts by weight of lactose, 50 parts by weight of crude cellulose, 2 parts by weight of magnesium stearate, 2 parts by weight of a perfume, and 700 parts by weight of mannitol are put, and the mixture is made to be powder in a usual method. Tablets are manufactured to have a diameter of 5 mm and a weight of 110 mg per tablet (containing 10 mg of the effective component) by pounding the powder using a rotary pounding machine. The effects for the prevention of hair loss are investigated by administering the tablets thus manufactured to 5 healthy adult males who are older than 20 years old and selected to be specimens three times a day (30 mg=3×10 mg).

TABLE 10

Evaluation of clinical experiments (5)-(Tertiary specimens)

|  | Time taken for the efficacy to be shown | | | | | |
|---|---|---|---|---|---|---|
|  | 3-5 days | 7 days | 14 days | 21 days | 28 days | Minor effect | Total |
| Total | 0 | 5 | 0 | 0 | 0 | 0 | 5 |
| Male | 0 | 5 | 0 | 0 | 0 | 0 | 5 |

TABLE 11

Evaluation of clinical experiments (6)-(Tertiary specimens)

|  | Degree of efficacy | | | | | |
|---|---|---|---|---|---|---|
|  | No effect | 10-20% | 20-40% | 40-60% | 60-80% | Greater than 90% | Total |
| Total | 0 | 0 | 0 | 0 | 2 | 3 | 5 |
| Male | 0 | 0 | 0 | 0 | 2 | 3 | 5 |

As shown in Tables 10 and 11, the results of investigation show that the effects for the prevention of hair loss are superior within one week in all of 5 people, and are improved greatly compared to the group to which 10 mg of the effective component is administered. In case of newly produced hairs, it is shown that their color and thickness are much stronger than those of old hairs.

EXAMPLE 6

Clinical Experiments to Study Effects of Epilation

Figure 5A:
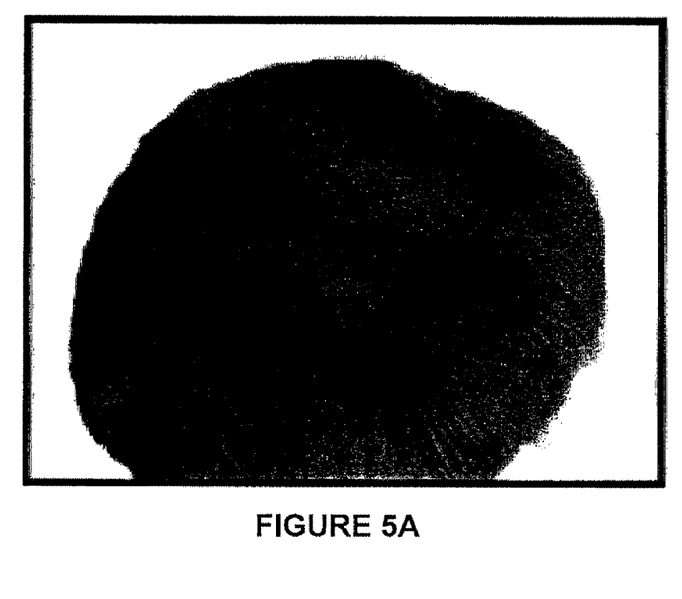
FIGS. 5A and 5B show a photographs in which clinical tests of a man before the administration of the composition of the present invention and after the continuous oral administration of the composition of the present invention for six months.
Figure 5B:
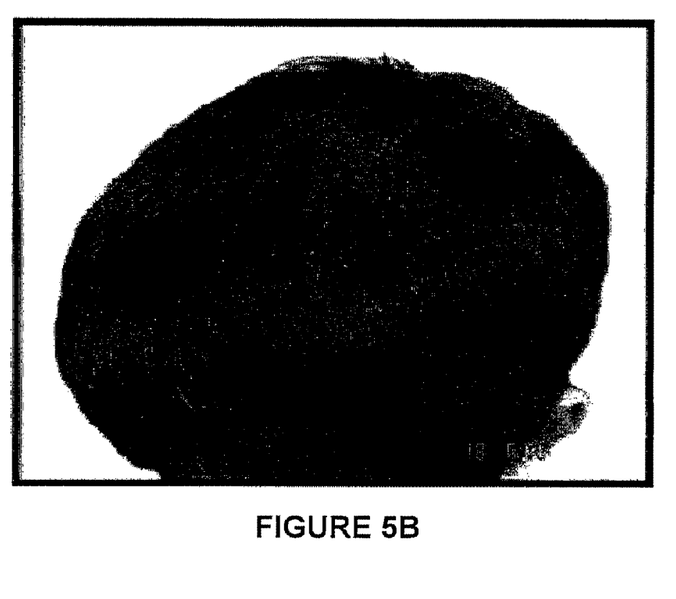

Into a mixer, 100 parts by weight of 2-[2-[4-[(4-chlorophenyl)phenylmethyl]-1-piperazinyl]ethoxy]-acetic acid dihydrochloride, 50 parts by weight of ascorbic acid, 50 parts by weight of corn starch, 50 parts by weight of lactose, 50 parts by weight of crude cellulose, 2 parts by weight of magnesium stearate, 2 parts by weight of a perfume, and 700 parts by weight of mannitol are put, and the mixture is made to be powder in a usual method. Tablets are manufactured to have a diameter of 5 mm and a weight of 110 mg per tablet (containing 10 mg of the effective component) by pounding the powder using a rotary pounding machine. The effects of epilation are investigated by administering the tablets thus manufactured once a day. FIG. 5A shows the state of hairs before the present invention is worked, and FIG. 6 shows the data on the measurement of the effects of epilation after the composition of the present invention is administered for six months. As shown in the photograph of FIG. 5B, the fact that the composition of the present invention shows considerable effects of epilation is readily evidenced with naked eyes.

INDUSTRIAL APPLICABILITY

The composition according to the present invention has a proven bio-stability throughout the world as an anti-allergic agent, anti-histamine, bronchodilator, and spasmolytic, but nothing has been reported until the present time as to its effects for the prevention of hair loss in androgenic alopecia, epilation, hair toning, hair growth, and female hirsutism, and the treatment of benign prostatic hyperplasia, which are the uses of the present invention. It is shown from the results of clinical experiments and in-vivo experiments using animals determining direct effects of the composition that the composition of the present invention is advantageous in that it has very superior activities for the prevention of hair loss, epilation, hair toning, hair growth, and female hirsutism, and for the treatment of benign prostatic hyperplasia; its safety is secured since active components, which are proven to be harmless to human bodies, are used; it is very easy to use the composition compared to applicable formulations owing to simple ways of administration such as oral administration; it is very convenient to use it since sufficient effects may be expected by administering once a day simply; it contains non-steroidal active materials; and there are shown no side effects such as sexual function disorder, etc. shown in the conventional oral epilation agents and prostatic hyperplasia treatment agents.

Further, the composition of the present invention is a safe composition having no problem of side effects reported yet in spite of its long-term use, which means that it conforms to the temporal trend in which it is critically necessary to have treatment agents for hair loss and diseases related to the prostate gland.

It will be apparent to those skilled in the art that various modifications and variations can be made in the disclosed products without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for the reduction of hair loss; for hair regrowth, hair toning or hair growth; or for the treatment of female hirsutism in a subject in need thereof, which comprises administering to the subject an effective amount of 2-[2-[4-[(4-chlorophenyl)phenylmethyl]-1-piperazinyl]ethoxy]-acetic acid or its pharmaceutically acceptable salt.

2. The method of claim 1, wherein said 2-[2-[4-[(4-chlorophenyl)-phenylmethyl]-1-piperazinyl]ethoxy]-acetic acid is in the form of a racemate or an optical isomer.

3. The method of claim 1, wherein said pharmaceutically acceptable salt is dihydrochloride.

4. The method of claim 1, wherein said 2-[2-[4-[(4-chlorophenyl)-phenylmethyl]-1-piperazinyl]ethoxy]-acetic acid or its pharmaceutically acceptable salt is administered orally or locally.

5. The method of claim 1, wherein said 2-[2-[4-[(4-chlorophenyl)-phenylmethyl]-1-piperazinyl]ethoxy]-acetic acid or its pharmaceutically acceptable salt is administered orally once to three times a day at an amount of 1 to 2,000 mg/day as 2-[2-[4-[(4-chlorophenyl)phenylmethyl]-1-piperazinyl]ethoxy]-acetic acid.

6. The method of claim 5, wherein said 2-[2-[4-[(4-chlorophenyl)-phenylmethyl]-1-piperazinyl]ethoxy]-acetic acid or its pharmaceutically acceptable salt is administered orally once to three times a day at an amount of 5 to 300 mg/day as 2-[2-[4-[(4-chlorophenyl)phenylmethyl]-1-piperazinyl]ethoxy]-acetic acid.

* * * * *